United States Patent
Hope et al.

(10) Patent No.: US 7,259,284 B2
(45) Date of Patent: *Aug. 21, 2007

(54) METHOD FOR MANUFACTURING HIGH VISCOSITY POLYALPHAOLEFINS USING IONIC LIQUID CATALYSTS

(75) Inventors: Kenneth D. Hope, Kingwood, TX (US); Donald W. Twomey, Kingwood, TX (US); Michael S. Driver, San Francisco, CA (US); Donald A. Stern, Kingwood, TX (US); J. Barry Collins, New Caney, TX (US); Thomas V. Harris, Benicia, CA (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 184 days.

This patent is subject to a terminal disclaimer.

(21) Appl. No.: 10/900,221

(22) Filed: Jul. 27, 2004

(65) Prior Publication Data

US 2005/0113621 A1    May 26, 2005

Related U.S. Application Data

(60) Continuation-in-part of application No. 10/078,759, filed on Feb. 19, 2002, now abandoned, which is a division of application No. 09/588,103, filed on May 31, 2000, now Pat. No. 6,395,948, and a continuation-in-part of application No. 10/420,261, filed on Apr. 22, 2003.

(60) Provisional application No. 60/374,528, filed on Apr. 22, 2002.

(51) Int. Cl.
*C07C 2/04* (2006.01)

(52) U.S. Cl. ............... 585/510; 585/512; 585/513; 585/514; 585/520

(58) Field of Classification Search ............... 585/510, 585/512, 513, 514, 520
See application file for complete search history.

(56) References Cited

U.S. PATENT DOCUMENTS 2,405,950 A    8/1946    Hanford (Continued)

FOREIGN PATENT DOCUMENTS

EP    0 791 643    8/1997

(Continued)

OTHER PUBLICATIONS

Bergman, Lee H., et al., Method and System to Add High Shear to Improve and Ionic Liquid Catalyzed Chemical Reaction, U.S. Appl. No. 10/978,792, filed Nov. 1, 2004, Specification & Drawings ( pages).

(Continued)

*Primary Examiner*—Tam M. Nguyen
(74) *Attorney, Agent, or Firm*—Conley Rose, P.C.; Rodney B. Carroll; K. KaRan Reed

(57) ABSTRACT

A process for preparing very high viscosity polyalphaolefins using an acidic ionic liquid oligomerization catalyst in the absence of an organic diluent and the products formed thereby. A method of continuously manufacturing a high viscosity polyalphaolefin product by introducing a monomer and an ionic liquid catalyst together into a reaction zone while simultaneously withdrawing from the reaction zone a reaction zone effluent that contains the high viscosity polyalphaolefin. The reaction zone is operated under reaction conditions suitable for producing the high viscosity polyalphaolefin product. The preferred high viscosity polyalphaolefin has a kinematic viscosity exceeding 8 cSt and is the reaction product of the trimerization, oligomerization, or polymerization of an alpha olefin or a mixture of one or more product thereof. The high viscosity polyalphaolefins are useful as lubricants or lubricant additives.

25 Claims, 5 Drawing Sheets

U.S. PATENT DOCUMENTS

| | | | |
|---|---|---|---|
| 3,647,912 A * | 3/1972 | Langer et al. .............. 585/524 |
| 4,827,064 A | 5/1989 | Wu |
| 5,087,782 A | 2/1992 | Perline |
| 5,196,574 A | 3/1993 | Kocal |
| 5,304,615 A | 4/1994 | Ambler et al. |
| 5,386,072 A | 1/1995 | Cozzi et al. |
| 5,502,018 A * | 3/1996 | Chauvin et al. ............. 502/213 |
| 5,550,304 A * | 8/1996 | Chauvin et al. ............. 585/512 |
| 5,731,101 A | 3/1998 | Sherif et al. |
| 5,824,832 A | 10/1998 | Sherif et al. |
| 5,891,830 A | 4/1999 | Koltermann et al. |
| 6,087,307 A | 7/2000 | Kaminski et al. |
| 6,395,948 B1 | 5/2002 | Hope et al. |
| 6,414,099 B1 * | 7/2002 | Hlatky et al. .............. 526/161 |
| 6,444,866 B1 * | 9/2002 | Commereuc et al. ....... 585/517 |
| 2002/0128532 A1 | 9/2002 | Hope et al. |
| 2003/0085156 A1 | 5/2003 | Schoonover |
| 2004/0005985 A1 | 1/2004 | Hope et al. |
| 2004/0030075 A1 | 2/2004 | Hope et al. |

FOREIGN PATENT DOCUMENTS

| | | |
|---|---|---|
| WO | WO95/21871 | 8/1995 |
| WO | WO95/21872 | 8/1995 |
| WO | WO88/06576 | 9/1998 |
| WO | WO99/38938 | 8/1999 |
| WO | WO 00/32658 | 6/2000 |
| WO | WO 00/41809 | 7/2000 |
| WO | WO 01/64622 | 9/2001 |
| WO | WO 03/089390 | 10/2003 |

OTHER PUBLICATIONS

Hope, Kenneth D., et al., Method and System to Contact an Ionic Liquid Catalyst with Oxygen to Improve a Chemical Reaction, U.S. Appl. No. 10/978,547, filed Nov. 1, 2004, Specification & Drawings ( pages).

Wasserscheid P. et al.; "Ionic Liquids—New Solutions for Transition Metal Catalysis"; Angewante Chemie International Edition; vol. 39, Oct. 27, 2000; pp. 3772-3789.

International Search Report, PCT/US 03/04838, Jun. 12, 2003, 4 pages.

PCT Written Opinion, PCT/US 03/04838, Apr. 8, 2004, 6 pages.

International Search Report, PCT/US 03/12823, Dec. 17, 2003, 5 pages.

PCT Written Opinion, PCT/US 03/12823, Jul. 26, 2004, 6 pages.

International Search Report, PCT/US 03/12821, Jan. 29, 2004, 7 pages.

PCT Written Opinion, PCT/US 03/12821, Feb. 18, 2004, 6 pages.

Schubert H.; "Mechanical Emulsification—New Developments and Trends"; AICHE National Meeting, Nov. 12, 2000.

International Search Report and PCT Written Opinion, PCT/US2004/036188, Feb. 23, 2005, 9 pages.

International Search Report and PCT Written Opinion, PCT/US2004/036410, Feb. 21, 2005, 7 pages.

* cited by examiner

METHOD FOR MANUFACTURING HIGH VISCOSITY POLYALPHAOLEFINS USING IONIC LIQUID CATALYSTS

CROSS-REFERENCE TO RELATED APPLICATIONS

This application is a continuation-in-part of U.S. patent application Ser. No. 10/078,729, filed Feb. 19, 2002 entitled "High Viscosity Polyalphaolefins Prepared with Ionic Liquid Catalyst," now abandoned, which in turn is a divisional patent application of U.S. patent application Ser. No. 09/588,103, filed May 31, 2000, now U.S. Pat. No. 6,395,948. This application is also a continuation-in-part of U.S. patent application Ser. No. 10/420,261, filed Apr. 22, 2003 entitled "Method for Manufacturing High Viscosity Polyalphaolefins Using Ionic Liquid Catalysts" which claims the benefit of and priority to provisional U.S. patent application Ser. No. 60/374,528, filed Apr. 22, 2002, which is related to U.S. patent application Ser. No. 10/420,182, entitled "Method for Manufacturing Ionic Liquid Catalysts." Each of the above-listed applications is hereby incorporated herein by reference in its entirety for all purposes.

FIELD OF THE INVENTION

The present invention relates to the preparation of high viscosity polyalphaolefins prepared using an ionic liquid catalyst. The present invention also relates to a continuous process for the manufacture of high viscosity polyalphaolefin products from an alpha olefin feedstock using an ionic liquid catalyst where the polyalphaolefin products have unique physical properties that make them useful as lubricants or lubricant additives.

BACKGROUND

Alpha olefins may be oligomerized to prepare synthetic lubricating oil base stocks which have desirable lubricating properties such as a low pour point and a high viscosity index (VI). However, many of these oligomerization products do not have the physical properties desired for certain applications, and they are often expensive to manufacture.

U.S. Pat. No. 4,827,064 discloses high viscosity polyalphaolefins that have high viscosity indices and low pour points. The high viscosity polyalphaolefins are characterized by a uniform molecular structure with low branch ratios. However, the polyalphaolefins are expensive to manufacture using conventional oligomerization processes.

U.S. Pat. No. 5,304,615 discloses a process for the polymerization of butenes using an ionic liquid as a catalyst, but the disclosure does not suggest a continuous process or the use of an ionic liquid composition derived from the combination of an alky-containing amine hydrohalide salt and a metal halide.

U.S. Pat. No. 5,731,101 discusses the possible use of low temperature ionic liquids as a catalyst for dimerization, oligomerization, and polymerization, but it does not specifically teach the oligomerization or polymerization of alpha olefins; and there is no suggestion of a continuous process using an ionic liquid to make polyalphaolefin products that are useful as lubricants or lubricant additives.

U.S. Pat. No. 5,824,832 is a continuation-in-part of U.S. Pat. No. 5,731,101 discussed above, and it focuses on the use of ionic liquids in the alkylation of aromatic molecules. The only exemplified reactions are those involving an aromatic compound, such as benzene and toluene. There is no suggestion of a continuous process using an ionic liquid to make a polyalphaolefin product.

EP 0791643 describes a process for oligomerizing alpha olefins, such as decene, using an ionic liquid catalyst to produce polyalphaolefins having a viscosity up to about 20 centistokes (cSt) at 100° C., but it does not teach the use of an ionic liquid composition derived from the combination of an alkyl-containing amine hydrohalide salt and a metal halide nor does it teach a continuous process. Additionally, the process taught in this application has not been shown to be suitable for making very high viscosity material, i.e., polyalphaolefins having a viscosity above 22 cSt at 100° C.

WO 95/21872 describes ternary compositions with ammonium halides are described in as being useful for olefinic oligomerization. Additional references discuss the use of imidazolium, pyridinium, or phosphonium as one component in the ionic liquid in addition to aluminum halide or gallium halide.

Considering the above discussed prior art, it is clear that there is a need for economical methods to produce high viscosity polyalphaolefins. Additionally, it is clear that there is a need for an economical process that utilizes the advantages of continuous processing for the manufacture of a polyalphaolefin product having certain desirable physical properties. Applicants have also found a continuous process for manufacturing polyalphaolefins having certain desirable properties.

SUMMARY OF THE INVENTION

The present invention is directed to a process for producing a high viscosity polyalphaolefin product comprising contacting a feed comprising one or more alpha olefins having from 6 to 18 carbon atoms with an effective oligomerizing amount of an acidic ionic liquid oligomerization catalyst, maintaining said feed and oligomerization catalyst under preselected oligomerization conditions for a sufficient time to oligomerize the alpha olefin to the polyalphaolefin product, and recovering the high viscosity polyalphaolefin product. As noted above, it has been found that high viscosity products may be obtained using the process of the present invention by carrying out the oligomerization reaction in the absence of organic diluent. Using the process of the invention, polyalphaolefins having viscosities in excess of 22 cSt and even in excess of 30 cSt may be readily prepared. In some embodiments, the feed consists essentially of one or more alpha olefins having from 4 to 14 carbon atoms. In other embodiments, the polyalphaolefin products are prepared from feeds comprising decene or dodecene.

The acidic ionic liquid oligomerization catalyst usually will be comprised of at least two components, and in most instances, it will be a binary catalyst, i.e., it will consist of only two components. The first component is a metal halide. In some embodiments, the first component is selected from the group consisting of an aluminum halide, an alkyl aluminum halide, a gallium halide, an alkyl gallium halide, a titanium halide, and an alkyl titanium halide. In other embodiments, the first component may be a combination of metal halides. In yet other embodiments, the first component is selected from the group consisting of an aluminum halide, an alkyl aluminum halide, a gallium halide, an alkyl gallium halide, a titanium halide, and an alkyl titanium halide either individually or in combinations thereof. In other embodiments, the first component of the ionic liquid oligomerization catalyst is an aluminum halide or an alkyl aluminum halide, such as, for example, aluminum trichloride. In other embodiments, the first component of the ionic liquid oligomerization catalyst is an aluminum halide or an alkyl aluminum halide, aluminum trichloride, and combinations thereof. Generally, the second component may be a quaternary ammonium, quaternary phosphonium, or tertiary sulfonium salt. In some embodiments, the second component is selected from one or more of hydrocarbyl substituted ammonium halides, hydrocarbyl substituted imidazolium halides, hydrocarbyl substituted pyridinium halides, alkylene substituted pyridinium dihalides, or hydrocarbyl substituted phosphonium halides. In other embodiments, the second component is an alkyl substituted ammonium halide, such as trimethylamine hydrochloride, or an alkyl substituted imidazolium halide, such as 1-ethyl-3-methyl-imidazolium chloride. The mole ratio of the two components will usually fall within the range of from 1:1 to 5:1 of said first component to said second component, and in some embodiments the mole ratio will be in the range of from 1:1 to 2:1.

The use of a binary catalyst composition consisting essentially of trimethylamine hydrochloride and aluminum trichloride is particularly advantageous for carrying out the process of the present invention due to the ease of preparation, the ready commercial availability of the components, and the relatively low cost.

The amount of catalyst present to promote the oligomerization of the alpha olefin should be not less than an effective oligomerizing amount, that is to say, the minimum amount of the catalyst necessary to oligomerize the alpha olefin to the desired product. This amount may vary to some degree depending on the composition of the catalyst, the ratio of the two components of the catalyst to one another, the feed, the oligomerization conditions chosen, the feed alpha olefin used, the desired polyalphaolefin properties (such as viscosity), and the like. However, in light of this disclosure, a determination of the effective catalytic amount should be well within the ability of one skilled in the art with no more than routine testing necessary to establish the amount needed to carry out the invention.

The present invention is also directed to the unique polyalphaolefin product prepared using the present invention. This product is characterized by a viscosity of not less than 22 cSt at 100° C., and more preferably will have a viscosity of at least 30 cSt at 100° C. In addition, the polyalphaolefin product will display a low pour point, preferably less than −30° C., and low volatility, preferably with a Noack volatility of 3 weight percent or less. Preferably, the product will have a dimer content of less than 2 weight percent.

The invention relates to a process for manufacturing a polyalphaolefin product having physical properties which make it either a desirable lubricant or lubricant additive for certain applications. In some embodiments, the polyalphaolefin product is made by a continuous process that includes the steps of introducing a monomer feed, comprising an alpha olefin, and a catalyst feed, comprising an ionic liquid catalyst, into a reaction zone while simultaneously withdrawing from the reaction zone a reaction effluent comprising the polyalphaolefin product.

Another embodiment of the invention relates to a method of controlling the viscosity of a polyalphaolefin product resulting from the ionic liquid catalyzed oligomerization of an alpha olefin by determining a correlation between the viscosity of the polyalphaolefin product and the concentration of the ionic liquid catalyst used in the oligomerization reaction. The correlation is used to set the concentration of the ionic liquid catalyst used in the reaction so as to provide the polyalphaolefin product having desired viscosity characteristics.

Still another embodiment of the invention relates to a novel polyalphaolefin composition produced by the ionic liquid catalyzed oligomerization of an alpha olefin to give such polyalphaolefin composition having unique physical properties.

DETAILED DESCRIPTION

Figure 1:
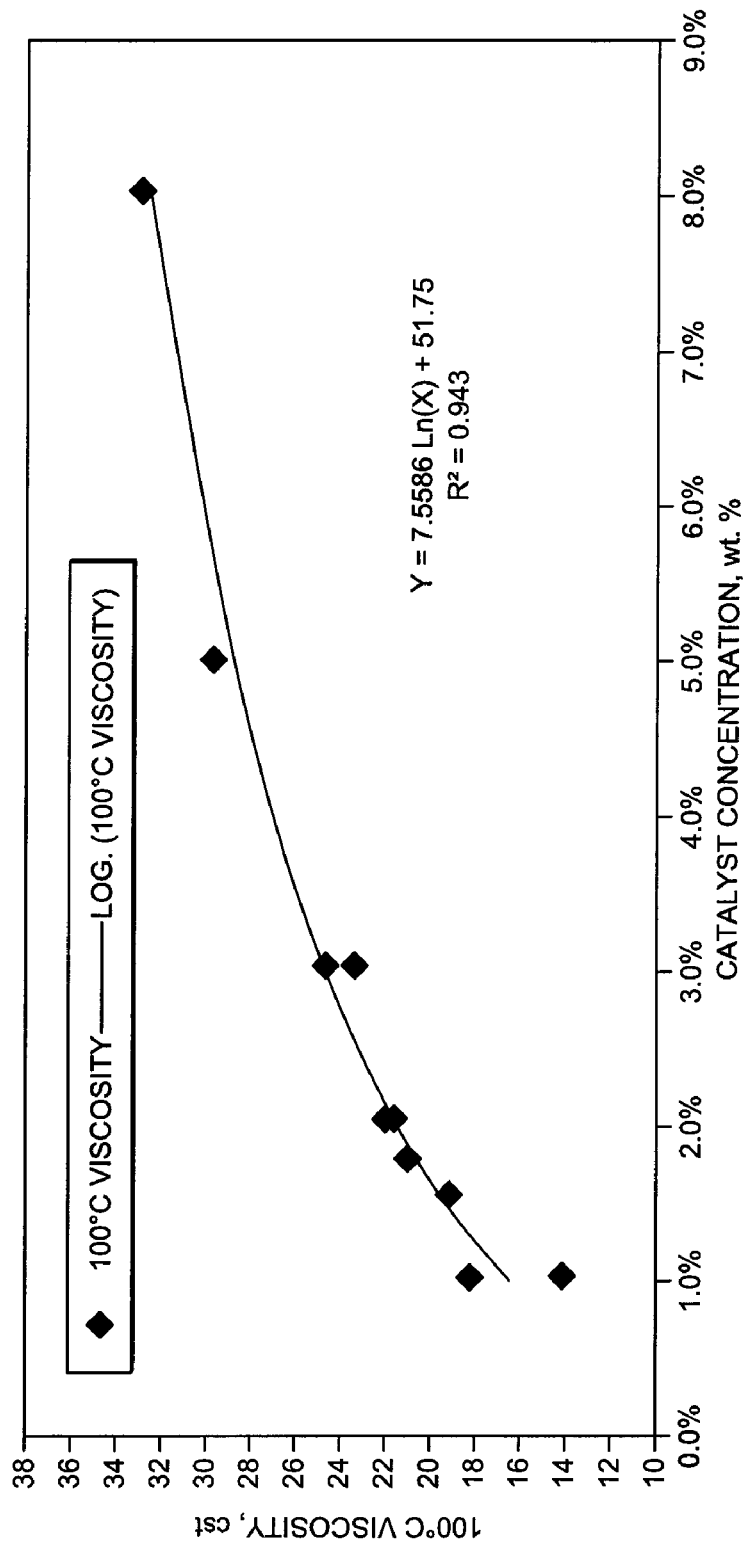
FIG. 1 is a plot of experimental data showing the correlation between the kinematic viscosity at 100° C. of a polyalphaolefin product produced from a continuous process for oligomerizing an alpha olefin monomer using an ionic liquid catalyst (aluminum trichloride trimethylamine hydrochloride) and the catalyst concentration as a percent, based on weight, of the monomer feedstock.

In the present application the term "high purity Normal Alpha Olefin(s)" or "high purity Normal Alpha Olefin fraction" is defined as, high purity, normal alpha olefin fractions made using an ethylene oligomerization process. As mentioned above in the present application, in the present application it is critical that the feed be free of any diluent or any significant impurities in order to achieve the desired result of a high viscosity polyalphaolefin product. As used herein, the term "polyalphaolefin product(s)" or "polyalphaolefin(s)" refers to a high purity Normal Alpha Olefin oligomerization product that is either a dimer, a trimer, a tetramer, higher oligomers, a polymer of the high purity Normal Alpha Olefin, or a mixture of any one or more thereof, each of which preferably has certain desired physical properties and, in particular, having the desired high viscosity properties all of which are more fully described below. The polyalphaolefin product may undergo subsequent processing such as distillation to remove undesired oligomers or polymer, hydrogenation to form a more stable product useful as a base oil stock, or both distillation and hydrogenation in any order or in any combination.

As used in this disclosure, the words "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the combination. The phrase "consisting of" is intended as a transition meaning the exclusion of all but the recited elements with the exception of only minor traces of impurities.

As used within this specification, the phrases "in the absence of any organic diluent," "in the absence of an organic diluent," "in the absence of organic solvents," and similar phrases refer to oligomerization conditions wherein the monomer concentration is not substantially reduced by non-reactive components. One skilled in the art recognizes that the terms "organic diluent" and "organic solvent" refer to specific compound(s) that are introduced to reduce the concentration of the reactive monomers or to serve specific function in the process, e.g. moderating the heat of reaction or providing fluidity to the reaction solution, and do not function as a reactant within the oligomerization. Thus, the phrases "in the absence of any organic diluent," "in the absence of an organic diluent," "in the absence of organic solvents," and similar phrases are not intended as limiting the invention to the complete absence of compounds that are impurities within the monomer feedstreams which under other circumstances or in greater quantities could be construed to act as a diluent. For example, while hexane could be an "organic diluent" or "organic solvent" under certain circumstances, the presence of 1.5 percent hexane as an impurity in the 1-hexene monomer stream does not substantially reduce the concentration of 1-hexene or serve a specific function within the reaction system and thus would not be excluded by the use of the phrases "in the absence of any organic diluent," "in the absence of an organic diluent," "in the absence of organic solvents," or similar terms.

As used within this specification, "short chain branching" refers to a side chain emanating from a tertiary or quaternary carbon atom having a methyl group within four carbon atoms from a tertiary or quaternary carbon atom. "Within four carbon atoms" describes the situation wherein if the tertiary or quaternary carbon atom is indicated as the 0 carbon atom, the methyl group carbon atom will be located at a carbon atom 1, 2, 3, or 4 carbon atoms from the tertiary or quaternary carbon atom.

Applicants have found that it is readily possible to make polyalphaolefins having very high viscosity using an ionic liquid catalyst by carrying out the oligomerization reaction in the absence of organic solvents which have hitherto been used as a diluent for the feed. Accordingly, Applicants have been able to make polyalphaolefins from feeds comprised primarily of olefins, such as decene and dodecene, having viscosities in excess of 22 cSt and even in excess of 30 cSt. Polyalphaolefins made using the process of the present invention also have been shown to display excellent viscosity index (VI) values, low pour points, and low Noack volatility values.

In some embodiments, the product polyalphaolefins have a pour point of less than −30° C. In other embodiments, the product polyalphaolefins have a pour point less than −40° C.

In some embodiments the polyalphaolefins have a viscosity index greater than 130. Alternatively, the polyalphaolefins have a viscosity index greater than 140; greater than 150; greater than 160; greater than 170.

In some embodiments the polyalphaolefin have a Noack volatility of less than or equal to 3 weight percent according to CEC L40 T87 or ASTM D5800 (ASTM has reviewed and adopted CEC L40 T87 as ASTM D5800). In other embodiments the polyalphaolefin have a Noack volatility of less than or equal to 2 weight percent according to CEC L40 T87 or ASTM D5800.

The inventive processes disclosed herein may be either continuous or batch. However, as noted herein, it is essential that the oligomerization reaction be conducted in the absence of any organic diluent. In carrying out the processes of the present invention, the alpha olefin feed may be added to the catalytic mixture or the catalyst may be added to the alpha olefin feed. In either case, the feed and the product formed during the oligomerization will form a separate phase from the ionic liquid which readily allows the two phases to be separated. To facilitate mixing of the catalyst and the feed, it is desirable either to stir the oligomerization mixture or to bubble the alpha olefin feed through the ionic liquid catalyst. Following completion of the oligomerization reaction, the mixing should be halted, and the product and residual feed should be allowed to form a distinct layer apart from the catalyst phase. In previous processes, the feed and product phase usually also contained an organic diluent, such as hexane. Applicants have discovered the presence of the organic diluent of the previous processes interferes with the oligomerization reaction and prevents the formation of the desired high viscosity polyalphaolefin product.

Some of the inventive processes disclosed herein for manufacturing a high viscosity polyalphaolefin product are unique in that they are continuous processes. Further embodiments of the inventive processes include methods involving the adjustment of certain process variables to provide for the control of the physical properties of the high viscosity polyalphaolefin product to give a polyalphaolefin product having desired properties. One embodiment of the inventive process includes the introduction of both a monomer feed that comprises at least one alpha olefin and an ionic liquid catalyst into a reaction zone and withdrawing from said reaction zone during the introduction of the monomer feed and ionic liquid catalyst into said reaction zone a reaction effluent that comprises a polyalphaolefin product.

The reaction zone of the process can be defined by any reaction means known in the art that provides for the contacting of the monomer feed with the ionic liquid under suitable reaction conditions maintained and controlled so as to provide for the reaction of the monomer feed to thereby give the polyalphaolefin product. The reaction zone is generally defined by a reactor vessel into which the monomer feed and ionic liquid catalyst are introduced. The monomer feed and ionic liquid catalyst can be introduced separately into the reaction zone as separate feed streams, or they can be introduced together as a premixed mixture; but, because the monomer feed and ionic liquid catalyst are generally immiscible fluids, it is preferred for the reactor to be equipped with a mixing or stirring means for mixing the monomer feed and ionic liquid catalyst to provide the desired intimate contact of the two fluids or to provide the preferred substantially homogenous mixture of monomer feed and ionic liquid catalyst. One type of reactor that suitably provides for the required mixing of the monomer feed and ionic liquid catalyst is known in the art as a continuous stirred tank reactor (CSTR).

The reaction conditions within the reaction zone are maintained so as to provide suitable reaction conditions for the dimerization, oligomerization or polymerization or any combination thereof of the alpha olefin of the monomer feed to give a polyalphaolefin product. The reaction pressure generally can be maintained in the range of from below atmospheric upwardly to 250 psia. Since the reaction is not significantly pressure dependent, it may be more economical to operate the reactor at a low pressure. In some embodiments, the reactor is operated at a pressure from atmospheric to 50 psia. In other embodiments, the reactor is operated at a pressure from atmospheric to 25 psia. The reaction temperature is to be maintained during the reaction so as to keep the reactants and catalyst in the liquid phase. The oligomerization reaction may take place over a wide temperature range. Generally, the reaction temperature range is from 0°

C. to 150° C. In some embodiments, the reaction temperature range is from 7° C. to 93° C. In other embodiments, the reaction temperature may be in the range of from 4° C. to 65° C., or alternatively, from 10° C. to 61° C. In other embodiments, the reaction is carried out at ambient temperature or slightly below. The oligomerization reaction is somewhat exothermic and it may be desirable to control the reaction temperature with internal or external cooling coils. In some embodiments, the temperature of the reaction mixture may be maintained below 50° C. Alternatively, the temperature of the reaction may be maintained below 30° C.

The residence time of the feed within the reaction zone has a small influence on the resultant reaction product but should provide sufficient time for the reaction to take place. As used herein, the term "residence time" is defined as being the ratio of the reactor volume to the volumetric introduction rate of the feeds, both the monomer feed and the ionic liquid catalyst feed, charged to or introduced into the reaction zone defined by a reactor. The residence time is in units of time. The reactor volume and feed introduction rate are such that the residence time of the total of the monomer feed and ionic liquid catalyst feed is generally in the range upwardly to 300 minutes. In some particular embodiments, the residence time is in the range of from 1 minute to 200 minutes. In other embodiments, the residence time is in the range of from 2 minutes to 120 minutes and, more preferably, from 5 minutes to 60 minutes.

Following completion of the oligomerization reaction, the organic layer containing the polyalphaolefin product and residual olefin feed is separated from the ionic liquid phase. The unreacted olefin and dimers may be removed from the product by conventional means, such as by distillation, and recycled back for further conversion. Likewise, the acidic ionic liquid catalyst that remains after recovery of the organic phase may be recycled to the oligomerization zone.

One feature of the inventive process is that polyalphaolefin reaction zone effluent has a low dimer content. In some embodiments, the polyalphaolefin reaction zone effluent has a dimer content of less than 5 weight percent. In other embodiments, the polyalphaolefin reaction zone effluent has a dimer content of less than 3 weight percent. In yet other embodiments, the polyalphaolefin reaction zone effluent has a dimer content of less than 2 weight percent.

Following recovery of the polyalphaolefin product, it is generally desirable to hydrogenate the unsaturated double bonds which remain in the product mixture. This is readily accomplished by conventional means well known to those skilled in the art. The hydrogenation of the unsaturated bonds is usually carried out with hydrogen in the presence of a hydrogenation catalyst such as, for example, catalyst containing nickel, palladium, platinum, cobalt or the like. In some embodiments, the polyalphaolefins have a bromine index of less than or equal to 800 mg/100 g according to ASTM D2710 after hydrogenation.

The applicants have discovered unexpectedly that small quantities of water increase the reactivity of the ionic liquid catalyst. Thus, in some embodiments, water may be present in the reaction zone. The amount of water present in the reaction zone may be controlled to maintain the reaction and avoid deactivating the ionic liquid catalyst. In an embodiment, the amount of water present in the reaction zone is from 0.1 to 50 ppm. In an embodiment, the amount of water present in the reaction zone is from 10 to 20 ppm based upon the weight of the total reactants within the reaction zone. In an embodiment, the amount of water present in the reaction zone is controlled such that the amount is less than an upper amount that is sufficient to deactivate the ionic liquid catalyst (e.g., formation of an undesirable amount of aluminum hydroxide species from aluminum trichloride) and greater than a lower amount that is insufficient to maintain the desired reaction (e.g., conversion of monomer feed to less than 20 weight percent) in the reaction zone.

The lower amount of water for a given ionic liquid catalyst composition may be determined experimentally by iteratively reducing the amount of water in the reaction zone and monitoring the monomer conversion until such conversion is unacceptable for the desired reaction. Conversely, the upper amount of water for a given ionic liquid catalyst composition may be determined experimentally by iteratively increasing the amount of water in the reaction zone and monitoring the catalyst deactivation until such deactivation is unacceptable for the desired reaction. What constitutes acceptable ionic liquid catalyst activity may depend upon, for example, the specific catalyst composition, the reaction conditions, and/or the types and properties (such as viscosity targets) for the end products being made.

In some embodiments, the maximum upper amount of water is the stoichiometric ratio of water that reacts with the catalyst to create a non-catalytic species thereof For an ionic liquid catalyst comprising aluminum trichloride that deactivates by reacting with water to form aluminum hydroxide, the maximum upper amount of water is a molar ratio of about 6 moles of water to each mole of aluminum trichloride.

The amount of water present in the reaction zone may be controlled by controlling the amount of water in the monomer feed to the reaction zone, controlling the amount of water in a gas located in a head space above the liquid components present in the reaction zone, or combinations thereof. The amount of water present in the ionic liquid catalyst, if any, is typically about constant and thus is not routinely adjusted or changed after initial control calibrations are performed.

In an embodiment where the amount of water present in the monomer feed is controlled, the amount of water present in the feed is from 5 to 15 ppm based upon the weight of the monomer feed. In an embodiment where the amount of water present in a head space gas is controlled, the monomer feed is dried to a water content of less than 1 ppm by weight and an amount of oxygen or wet gas such as moist nitrogen is added to the reaction zone to control the amount of water therein. The moist nitrogen may be produced, for example, by bubbling dry nitrogen through water. The oxygen may be pure oxygen, air, dried air, oxygen enriched air, other oxygen sources such as a process stream, or combinations thereof, and the stream of oxygen, for example dried air, may have less than 1 ppm of water by weight therein.

In an embodiment where the monomer feed is dried to less than 1 ppm by weight and the head space gas is dry nitrogen, the amount of water present in the reaction zone may be insufficient to maintain the desired reaction in the reaction zone, that is the conversion of the monomer feed was less than 20 weight percent. In such an embodiment, the weight percent conversion of monomer feed can be increased by increasing the amount of water present in the reaction zone as discussed previously, for example by adding air or moist nitrogen to the reaction zone head space or by other methods as known to those skilled in the art. Stated alternatively, an amount of water can be added to the ionic liquid catalyst in a manner described previously to activate the catalyst and thereby increase the weight percent conversion of monomer feed, provided however that such amount of added water is less than an amount that undesirably deactivates the catalyst.

Without intending to be bound by theory, it is believed that the ionic liquid catalysts require the presence of a proton donor such as an acid, and that water present or formed in the reaction zone reacts with the catalyst (e.g., aluminum trichloride) to form hydrogen chloride, which serves as a proton donor to the remaining catalyst. In an embodiment, an acid, for example hydrogen chloride or other acids such a Bronsted acid or a Lewis acid, is added directly to the ionic liquid catalyst. For example, hydrogen chloride may be added directly to the ionic liquid catalyst by bubbling hydrogen chloride gas through the ionic liquid catalyst or by any other methods as known to those skilled in the art.

The rate of introduction of ionic liquid catalyst into the reaction zone relative to the rate of introduction of monomer feed is an important feature of the inventive continuous process in that the control of the catalyst concentration can be used to control certain of the physical properties of the polyalphaolefin product. Thus, in one embodiment of the inventive process the weight ratio of ionic liquid catalyst to monomer feed is set so as to provide a polyalphaolefin product having desired physical properties. Generally, the weight ratio of ionic liquid catalyst to monomer feed is in the range upwardly to 1:1. In some embodiments, the weight ratio of ionic liquid to monomer feed is in the range from 0.01:100 to 25:100. In other embodiments, the weight ratio of ionic liquid catalyst to monomer feed introduced into the reaction zone of the process is in the range of from 0.1:100 to 20:100, or alternatively, in the range of from 0.1:100 to 15:100.

The monomer feedstock that is introduced into the reaction zone of the process comprises at least one alpha olefin hydrocarbon. In some embodiments, the monomer feed is substantially all alpha olefin. In other embodiments, the alpha olefins in the monomer feed comprise at least 95 weight percent of the monomer feed, or at least 99 weight percent of the monomer feed. The alpha olefins, which are also known as 1-olefins or 1-alkenes, suitable for use as the monomer feed of the process can have from 4 to 20 carbon atoms and include, for example, 1-butene, 1-pentene, 1-hexene, 1-octene, 1-nonene, 1-decene, 1-undecene, 1-dodecene, 1-tridecene and 1-tetradecene, 1-pentadecene, 1-hexadecene, 1-heptadecene, octadecene, 1-nonadecene and 1-eicosene. In some embodiments, the monomer feed comprises one or more one alpha olefins having from 6 to 20 carbon atoms. Alternatively, the monomer feed comprises one or more alpha olefins having from 6 to 14 carbon atoms; having from 8 to 12 carbon atoms. In other embodiments, the alpha olefins of the monomer feed have from 4 to 14 carbon atoms. In other embodiments, the alpha olefins of 1-decene and 1-dodecene provide for a polyalphaolefin product resulting from the inventive process described herein that have especially desirable physical properties. In other embodiments, the alpha olefins of the monomer feed consist essentially of 1-decene, 1-dodecene, or mixtures thereof. In other embodiments, the feed consists essentially of one or more alpha olefins having from 4 to 14 carbon atoms in the molecule. Alternatively, the feed consists essentially of one or more alpha olefins having from 6 to 14 carbon atoms; from 8 to 12 carbon atoms. In other embodiments, the alpha olefin feed contains 1-decene and 1-dodecene. While the feed may consist of a mixture of different alpha olefins, it is essential that the feed not contain any organic diluent.

As explained above and as further illustrated in the examples below, it has been found that the presence of an organic diluent interferes with the oligomerization reaction and prevents the formation of the desired high viscosity polyalphaolefin product. This differs from the prior processes which included an organic diluent, such as hexane or heptane, as part of the organic phase of the reaction mixture.

The reactor effluent withdrawn from the reaction zone of the inventive process generally can comprise the polyalphaolefin product of the process and the ionic liquid catalyst. The reactor effluent can further comprise a dimer of the alpha olefin in the monomer feed and the unreacted monomer, if any. The polyalphaolefin product can be separated from the other components of the reactor effluent including the ionic liquid catalyst, and, optionally, the unreacted monomer and dimers formed during the reaction of the monomer feed. The separated polyalphaolefin product may further be processed by methods such as hydrogenation to impart other desired properties. The polyalphaolefin product can include dimers, trimers, tetramers, higher oligomers, polymers, or mixture of any one or more thereof of the alpha olefin contained in the monomer feed. Such dimers, trimers, tetramers, higher oligomers, polymers, or mixture of any one or more thereof may comprise molecules having from 12 to over 1300 carbon atoms.

A particularly preferred polyalphaolefin product of the process is that manufactured, using the inventive process, from 1-decene, 1-dodecene, or a combination thereof. The polyalphaolefin products from these feedstocks are especially significant in that they have unique physical properties. Typical ranges for the various physical properties of the polyalphaolefin product and the relevant test methods for determining the physical properties are presented in the following Table of "Product Physical Properties."

| Product Physical Properties | | | | |
|---|---|---|---|---|
| Test | Units | Test Method | Value | |
| Kinematic Viscosity at 100° C. | cSt | ASTM D445 | Min | 12.0 |
| | | | Max | 35.0 |
| Bromine Index | mg/100 g | ASTM D2710 | Max | 800 |
| Volatility, Noack | wt % | CEC L40 T87 | Max | 2.0 |
| Flash Point | ° C. | ASTM D92 | Min | 245 |
| Fire Point | ° C. | ASTM D92 | Min | 290 |
| Pour Point | ° C. | ASTM D97 | Max | −30 |
| Polydispersity Index | | | Max | 3.5 |
| | | | Min | 1.0 |
| Weight Average Molecular Weight | | | Min | 170 |
| | | | Max | 18200 |

Presented in FIG. 1 is an exemplary plot showing the correlation between the kinematic viscosity at 100° C. of the alpha olefin product produced from a continuous process for oligomerizing an alpha olefin monomer using an ionic liquid catalyst (aluminum trichloride trimethylamine hydrochloride) and the ionic liquid catalyst concentration. The correlation is believed to be unexpected and can be used in the control of the kinematic viscosity of a polyalphaolefin product produced by the ionic liquid catalyzed oligomerization of alpha olefin. A determination is first made of the correlation between the weight ratio of ionic liquid catalyst to monomer feed and the kinematic viscosity of the polyalphaolefin product resulting from the oligomerization reaction. This correlation is then utilized to determine the concentration of ionic liquid catalyst necessary for providing the polyalphaolefin product having desired viscosity properties.

Generally, the kinematic viscosity at 100° C. of the polyalphaolefin product exceeds 8 cSt, but it is desirable for the kinematic viscosity at 100° C. to exceed 12 cSt. In some embodiments, the kinematic viscosity of the polyalphaolefin product exceeds 15 cSt, and in other embodiments, it exceeds 18 cSt. Alternatively, the kinematic viscosity of the polyalphaolefin product is not less than 22 centistokes at 100° C.; not less than 30 centistokes at 100° C. The desirable range for kinematic viscosity at 100° C. of the polyalphaolefin product is thus from 8 cSt to 40 cSt. Alternatively, the range for kinematic viscosity at 100° C. of the polyalphaolefin product is from 12 cSt to 35 cSt; from 15 cSt to 40 cSt; from 15 cSt to 30 cSt; from 22 cSt to 40 cSt; or from 22 cSt to 35 cSt.

One unique feature of the inventive polyalphaolefin product is that it has a low polydispersity index while having a high viscosity. It is desirable for the polydispersity index of the polyalphaolefin product to be as close to one as possible; since it is desirable for the polyalphaolefin product to have a narrow range of molecular weight. As used herein, the term polydispersity index refers to the ratio of weight average molecular weight ($M_w$) to number average molecular weight ($M_n$). The polydispersity index is an indication of the breadth of the molecular weight range with a value of one for the polydispersity index indicating that all the molecules in the polyalphaolefin product have the same molecular weight.

Generally, the polydispersity index of the polyalphaolefin product should be in the range of 1.0 to 3.5. In other embodiments, the polydispersity index of the polyalphaolefin product is in the range of from 1.0 to 3.0; in the range from 1.0 to 2.5; in the range of 1.0 to 2.0. In some embodiments, the polydispersity index of the polyalphaolefin product is in the range of from 1.0 to 3.5 when the polyalphaolefin product has a high kinematic viscosity at 100° C. exceeding 8 cSt. In yet other embodiments, the polydispersity index of the polyalphaolefin product is less than 3.0 and, therefore, in the range of from 1.0 to 3.0, when the kinematic viscosity at 100° C. exceeds 12 cSt, or exceeds 15 cSt, or alternatively exceeds 18 cSt. Alternatively, the polydispersity index of the polyalphaolefin product is in the range of from 1 to 2.5 when the polyalphaolefin product has a high kinematic viscosity at 100° C. so that it exceeds 12 cSt, 15 cSt, or alternatively 18 cSt. In some embodiments, the polydispersity of the polyalphaolefin product is in the range of from 1 to 2.5 when the polyalphaolefin product has a kinematic viscosity at 100° C. from 8 cSt to 40 cSt. Alternatively, the polydispersity of the polyalphaolefin product is in the range of from 1 to 2.5 when the polyalphaolefin product has a kinematic viscosity at 100° C. from 12 cSt to 35 cSt; 15 cSt to 40 cSt; from 15 cSt to 30 cSt; from 22 cSt to 40 cSt; or from 22 cSt to 35 cSt.

As described above, the polydispersity index is defined as the ratio of the weight average molecular weight to number average molecular weight both of the polyalphaolefin product. The weight average molecular weight has a meaning understood by those skilled in the art to be the summation of the weight fraction of each molecular species times its molecular weight. The number average molecular weight is understood to mean the summation of the mole fraction of each molecular species times its molecular weight.

The weight average molecular weight of the polyalphaolefin product can be in the range of from 170 to 18,200. In some embodiments the weight average molecular weight is in the range of 200 to 10,000, in the range of 210 to 8,000, or alternatively in the range of 250 to 3,000. In other embodiments, the weight average molecular weight of the polyalphaolefin product that has a low polydispersity index described herein while having a high viscosity, described herein, is between 210 and 8,000, alternatively, the weight average molecular weight of the polyalphaolefin product is in the range of from 250 to 3,000.

Without intending to be bound by theory, the applicants believe that the inventive processes produce polyalphaolefin products under cationic oligomerization conditions similar to the polyalphaolefin production conditions for molecular cationic polymerization catalysts (e.g. $BF_3$+promoter) or Zeigler-type catalysts. Under cationic oligomerization conditions olefin isomerization, oligomer rearrangement, or both may occur as described Shubkin et. Al., Ind. Eng. Chem. Prod. Res. Dev. 1980, 19, pp. 15-19 and Onopchenko et. al., Ind. Eng. Chem. Prod. Res. Dev. 1983, 22, pp. 182-191 the disclosures of which are incorporated by reference in their entirety. These processes produce polyalphaolefin products that have measurable amounts of short chain branching. However, unlike the polyalphaolefins produced from cationic polymerization or Zeigler-type catalysts, the inventive polyalphaolefin production processes produce polyalphaolefin products that have a molecular weight distribution between 500 and 2000 upon removal of the unreacted monomer and the dimer products. Additionally, the inventive polyalphaolefin process produces polyalphaolefin products having 100° C. viscosities, pour points, polydispersity indexes, Noack volatilities, and other properties as described herein.

The inventive polyalphaolefin production processes do not produce polyalphaolefins via head-to-tail alpha olefin oligomerization as described in U.S. Pat. No. 4,827,064 and do not have a highly regular structure obtained by head-to-tail oligomerization consisting essentially of the repeating unit:

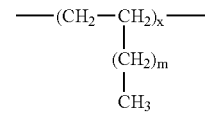

wherein m ranges from 3 to 17.

The presence or absence of the regular repeating structure due to head-to-tail alpha olefin incorporation, and conversely the absence of the regular repeating structure, can be determined by a number of methods. Applicable methods include the determination of the polyalphaolefin product branching ratio, the determination of the number of different methyl groups within the polyalphaolefin product, the presence of short chain branching within the polyalphaolefin product, or determining the mole % of methyl groups resulting from short chain branching within the polyalphaolefin product.

Figure 3:
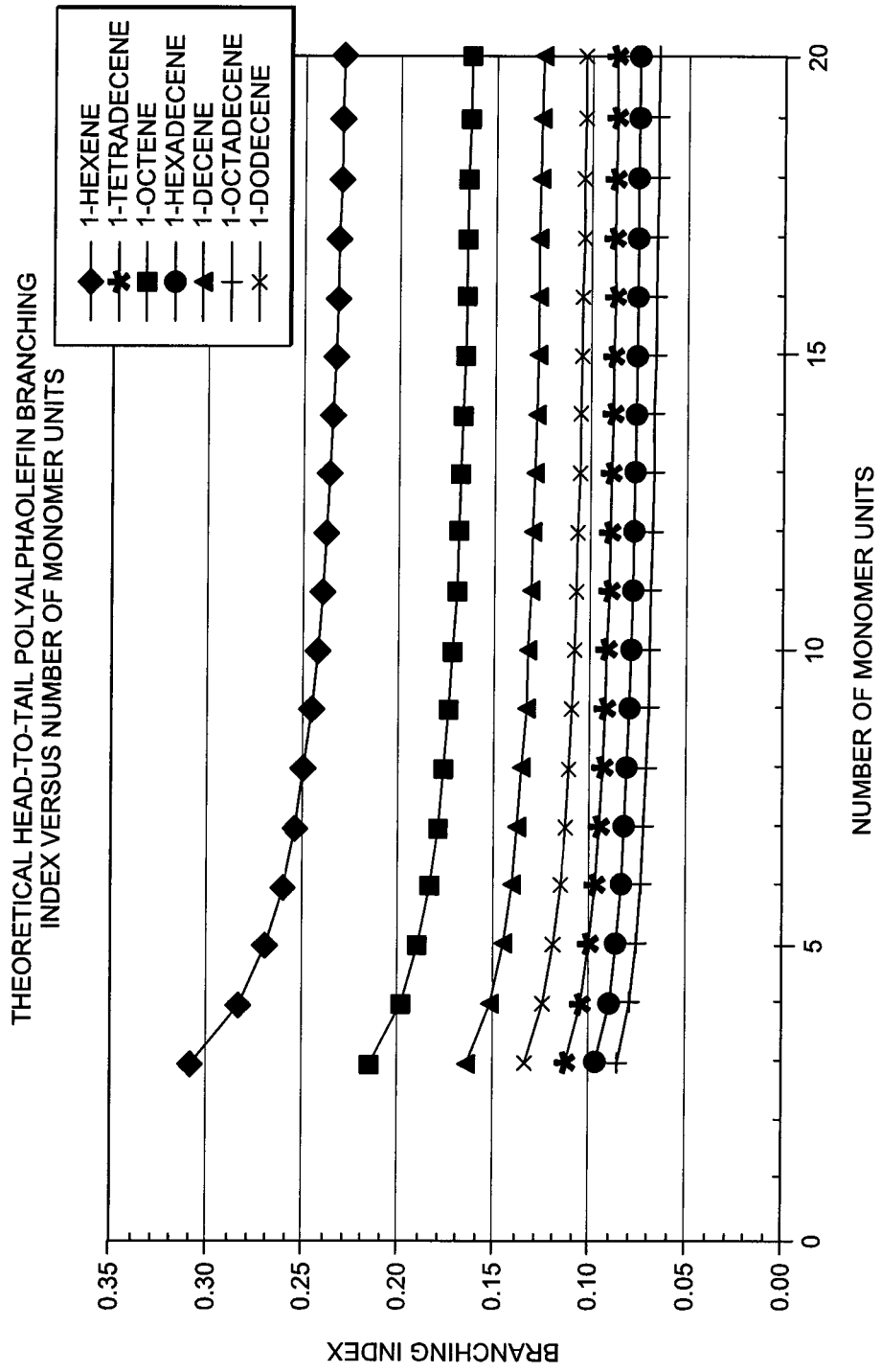
FIG. 3 illustrates the effect that alpha olefin feed carbon number and the number of monomer units incorporated into the polyalphaolefin product have upon the branch ratio of a polyalphaolefin product having a regular repeating structure.

The branching ratio as given by the equation $$\text{branching ratio} = \frac{\text{weight fraction methyl groups}}{1 - (\text{weight fraction methl groups})}$$

can be determined by infrared spectroscopy as discussed in "Standard Hydrocarbon of High Molecular Weight", Analytical Chemistry, Vol. 25 no. 10 pp. 1466-1470 (1953), or using $^{13}C$ NMR integration areas. In theory, polyalphaolefin product incorporating x monomer units having n carbon atoms per monomer unit produced by head to tail oligomerization will have the structure below:

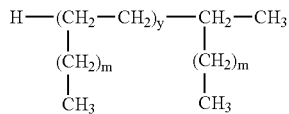

where y+1=x and m+3=n. Barring significant (greater than 5 mole percent) non-head-to-tail oligomerization, head-to-tail oligomerization produces a polyalphaolefin molecule containing x monomer units and x+1 methyl groups. Thus, the theoretical weight fraction of methyl groups in the polyalphaolefin molecule is given by the equation:

$$\frac{(x+1)*15}{(x*n*14)+2}$$

where x is the number of oligomer units within the polyalphaolefin molecule and n is the number of carbon atoms in the alpha olefin used to produce the polyalphaolefin. Thus, the theoretical branch ratio of polyalphaolefin molecule produced by head-to-tail oligomerization would have a branch ratio given by the equation:

$$\text{Branch ratio} = \left[\frac{(x+1)*15}{(x*n*14)+2}\right] \bigg/ \left\{1 - \left[\frac{(x+1)*15}{(x*n*14)+2}\right]\right\}$$

where x is the number of monomer units within the polyalphaolefin molecule and n is the number of carbon atoms in the alpha olefin used to produce the polyalphaolefin molecule. Using the equation above, FIG. 3 illustrates the point that the branch ratio of a polyalphaolefin molecule produced by head-to-tail oligomerization depends upon the number of monomer units incorporated into the polyalphaolefin molecule and the carbon number of the alpha olefin used to produce the polyalphaolefin molecule. FIG. 3 also indicates that the branch ratio of a polyalphaolefin molecule produced by head-to-tail oligomerization decreases with increasing monomer incorporation (increasing molecular weight) and decreases with increasing number of carbon atoms in the alpha olefin used to produce the polyalphaolefin.

The branch ratio of a head-to-tail polyalphaolefin product comprised of mixtures of polyalphaolefin molecules having different number of monomer incorporated therein may be calculated by the equation:

$$\text{branch ratio} = \sum_{2}^{x} Q_x * \left\{\left[\frac{(x+1)*15}{(x*n*14)+2}\right] \bigg/ \left\{1 - \left[\frac{(x+1)*15}{(x*n*14)+2}\right]\right\}\right\}$$

where $Q_x$ is weight fraction of the oligomer having x monomer units and n equals the number of carbon atoms in the alpha olefin used to produce the polyalphaolefin. The $Q_x$s may be determined by methods know to those skilled in the art (e.g. gas chromatography and gel permeation chromatography). Similarly, the branch ratios of alpha olefin oligomers produced from mixtures of alpha olefins may be calculated using the equation herein and methods known to those skilled in the art. The branch ratios can also be correlated to product viscosities using data available to those skilled in the art.

The inventive processes described herein produce product alpha olefins having branch ratios exceeding the theoretical branch ratio of polyalphaolefin product produced by methods giving regular head to tail oligomerization. In some embodiments, the product alpha olefins exceed the theoretical branch ratio of polyalphaolefin products produced by methods giving regular head to tail oligomerization by 10 percent; 15 percent; 20 percent; 25 percent; 35 percent; 45 percent. The theoretical branch ratio may be experimentally determined utilizing methods based upon a method selected from the group consisting of infrared spectroscopy and $^{13}C$ NMR spectroscopy. In other embodiments, the polyalphaolefin product has a branch ratio greater than or equal to 0.19; greater than or equal to 0.20.

The repeating structure of the polyalphaolefin produced by head-to-tail oligomerization also indicates that there is only one short chain branch per polyalphaolefin molecule. In contrast and without intending to be bound by theory, cationic oligomerization results in an average of more than one short chain branch per polyalphaolefin molecule due to feed alpha olefin isomerization, polyalphaolefin rearrangement, or both. Thus, the inventive processes produce polyalphaolefins that have more than one short chain branch per polyalphaolefin molecule and more that one kind of short chain branch. The presence of these types of short chain branches may be determined by observing the number of methyl groups other than the long chain methyl groups detected by $^{13}C$ NMR spectroscopy. In some embodiments, the polyalphaolefin product comprises at least 2 different short chain branches observable by $^{13}C$ NMR. In other embodiments, the polyalphaolefin product comprises at least 3 different short chain branches observable by $^{13}C$ NMR. In other embodiments, the polyalphaolefin product comprises at least 4 different short chain branches observable by $^{13}C$ NMR. In yet other embodiments, the polyalphaolefin comprise the number of short chain branches observable by $^{13}C$ NMR described herein and have a 100° C. Kinematic viscosity as described herein.

Yet another difference between the polyalphaolefins produced by the inventive process and polyalphaolefin produced from head-to-tail oligomerization is that the inventive process produces polyalphaolefin that have a measurable percentage of methyl groups resulting from short chain branching. The percent of methyl groups resulting from short chain branching may be determined by $^{13}C$ NMR spectroscopy using the equation:

$$\frac{100 * {}^{13}C \text{ integral area of short chain methyl groups}}{\text{total } {}^{13}C \text{ integral area of all methyl groups}}$$

In some embodiments, the polyalphaolefins have at least 3 percent short chain branching. In other embodiments, the polyalphaolefins have at least 5 percent short chain branching. Alternatively, the polyalphaolefins have at least 8 percent short chain branching; at least 10 percent short chain branching; at least 15 percent short chain branching.

Ionic liquid compositions suitable for use in the inventive process are complexes of two components that form compositions that are liquid under the reaction conditions of the inventive process. The ionic liquid compositions may be characterized by the general formula $Q^+A^-$, wherein $Q^+$ comprises a quaternary ammonium, quaternary phosphonium, or quaternary sulfonium, and $A^-$ comprises a negatively charged ion such as $Cl^-$, $Br^-$, $OCl_4^-$, $NO_3^-$, $BF_4^-$, $BCl_4^-$, $PF_6^-$ $SbF_6^-$, $AlCl_4^-$, $Al_2Cl_7^-$, $ArF_6^-$, $TaF_6^-$, $CuCl_2^-$, $FeCl_3^-$, $SO_3CF_3^-$, $SO_3C_7^-$, 3-sulfurtrioxyphenyl, or a combination thereof.

In some embodiments, the ionic liquid catalyst is the complex resulting from the combination of a metal halide and an alkyl-containing amine hydrohalide salt. Such compositions are described in detail in U.S. Pat. No. 5,731,101, the disclosure of which is incorporated herein by reference. It has been found that the use of such ionic liquid compositions provides for polyalphaolefin end-products having certain desirable and novel physical properties that make them especially useful in various lubricant or lubricant additive applications.

The metal halides that can be used to form the ionic liquid catalyst used in this invention are those compounds which can form ionic liquid complexes that are in liquid form at the reaction temperatures noted above when combined with an alkyl-containing amine hydrohalide salt. Generally, the metal halides are covalently bonded metal halides. Possible suitable metals which can be selected for use herein include those from Groups VIII, IB, IIB, IIIA, and IVB of the Periodic Table of the Elements, CAS version. More specifically, the metal of the metal halides can be selected from the group consisting of aluminum, gallium, iron, copper, zinc, indium, and titanium either individually or in any combination thereof. In some embodiments, the metals are aluminum and gallium. In another embodiment, the metal is aluminum. In some embodiments, the metal halides include those selected from the group consisting of aluminum halide, alkyl aluminum halide, gallium halide, and alkyl gallium halide. In other embodiments, the metal halide is an aluminum halide or alkyl aluminum halide. In yet another embodiment, metal halide as a reactant for use in the inventive process is aluminum trichloride.

The presence of the first component should give the ionic liquid a Lewis (or Franklin) acidic character. Generally, the greater the mole ratio of the first component to the second component, the greater the acidity of the ionic liquid mixture. When aluminum trichloride and trimethylamine hydrochloride are used as the first and second components, respectively, of the acidic ionic liquid oligomerization catalyst, they preferably will be present in a mole ratio of from 1:1 to 2:1.

The alkyl-containing amine hydrohalide salts that can be used to form the ionic liquid catalyst used in this invention include monoamines, diamines, triamines and cyclic amines, all of which include one or more alkyl group and a hydrohalide anion. The term alkyl is intended to cover straight and branched alkyl groups having from 1 to 9 carbon atoms. In some embodiments, the alkyl-containing amine hydrohalide salts useful in this invention have at least one alkyl substituent and can contain as many as three alkyl substituents. In other embodiments, the second component are those quaternary ammonium halides containing one or more alkyl moieties having from 1 to 9 carbon atoms, such as, for example, trimethylamine hydrochloride, or hydrocarbyl substituted imidazolium halides, such as, for example, 1-ethyl-3-methyl-imidazolium chloride. The quaternary ammonium halides are distinguishable from quaternary ammonium salts which have all four of their substituent positions occupied by hydrocarbyl groups.

Generally, the quaternary ammonium halides that are contemplated herein have the generic formula $R_3N.HX$, where at least one of the "R" groups is alkyl, preferably an alkyl of from one to eight carbon atoms (preferably, lower alkyl of from one to four carbon atoms) and X is halogen. In some embodiments, the halogen is a chloride. If each of the three R groups is designated $R_1$, $R_2$ and $R_3$, respectively, the following possibilities exist in certain embodiments: each of $R_1$—$R_3$ can be lower alkyl optionally interrupted with nitrogen or oxygen or substituted with aryl; $R_1$ and $R_2$ can form a ring with $R_3$ being as previously described for $R_1$; $R_2$ and $R_3$ can either be hydrogen with $R_1$ being as previously described; or $R_1$, $R_2$ and $R_3$ can form a bicyclic ring. In some embodiments, these groups are methyl or ethyl groups. If desired the di-and tri-alkyl species can be used. In some embodiments, the alkyl containing amine hydrohalide salt are those compounds where the R groups are either hydrogen or an alkyl group having 1 to 4 carbon atoms, and the hydrohalide is hydrogen chloride, an example of which is trimethylamine hydrochloride. Alternatively, one or two of the R groups can be aryl, but this is not preferred. The alkyl groups, and aryl, if present, can be substituted with other groups, such as a halogen. Phenyl and benzyl are representative examples of possible aryl groups to select. However, such further substitution may undesirably increase the viscosity of the melt. Therefore, it is highly desirable that the alkyl groups, and aryl, if present, be comprised of carbon and hydrogen groups, exclusively. Such short chains are preferred because they form the least viscous or the most conductive melts. Mixtures of these alkyl-containing amine hydrohalide salts can be used.

Figure 2:
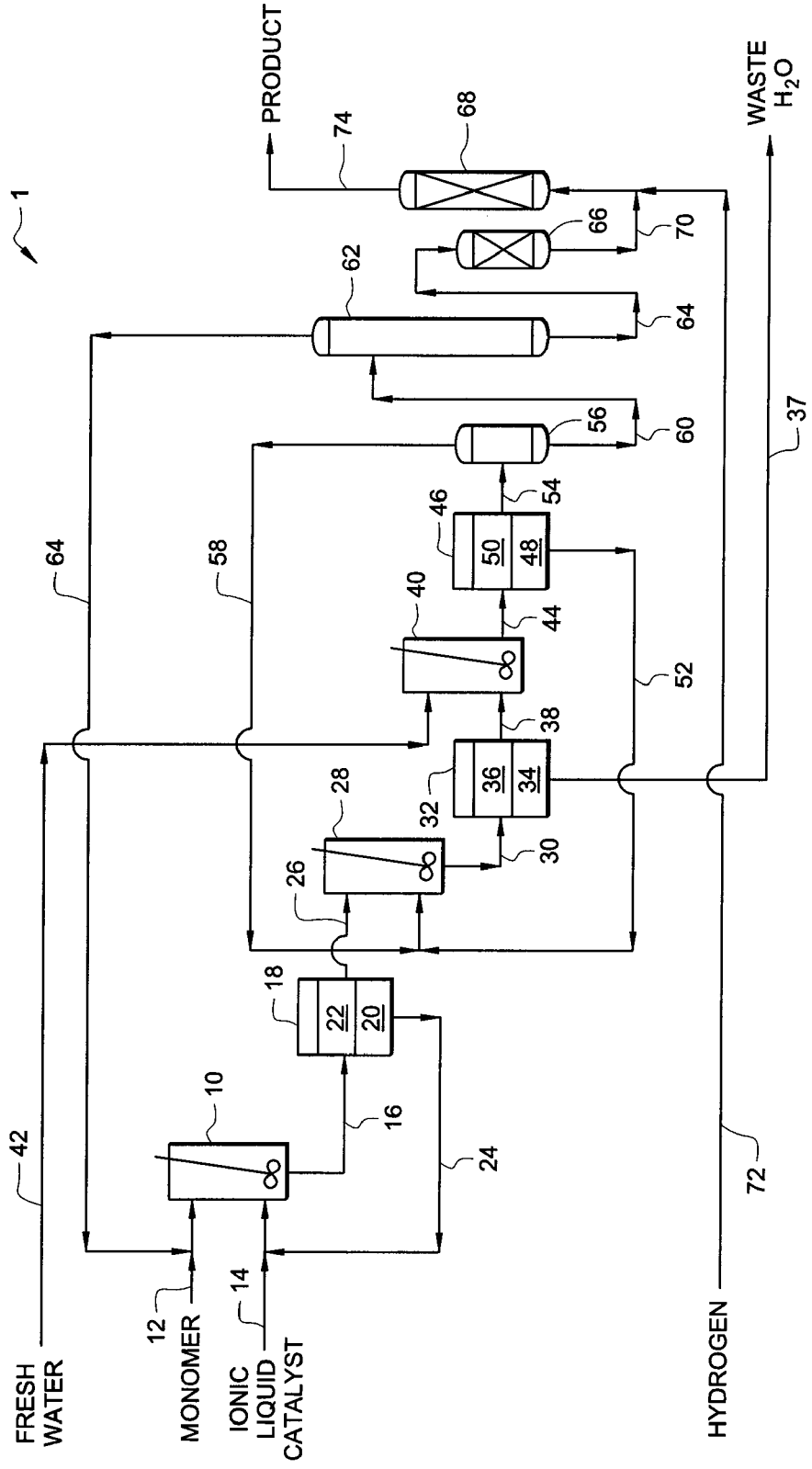
FIG. 2 is a process flow schematic of one embodiment of the process for manufacturing a polyalphaolefin product which also depicts further steps of product separation and hydrogenation of a separated polyalphaolefin product.

Now referring to FIG. 2 wherein is represented production process 1 for manufacturing a hydrogenated polyalphaolefin product. Monomer feed and the recycled monomer and dimmer, which are more fully described herein, are introduced or charged to continuous stirred tank reactor (CSTR) 10 by way of conduit 12. Makeup ionic liquid catalyst and recycled ionic liquid catalyst feed, which are more fully described herein, are introduced or charged to CSTR 10 by way of conduit 14. The monomer and ionic liquid catalyst feeds are simultaneously introduced into the CSTR 10 while the reactor effluent from CSTR 10 is, simultaneously with the introduction of the feeds, withdrawn from CSTR 10 through conduit 16. by way of conduit 14. The monomer and ionic liquid catalyst feeds are simultaneously introduced into the CSTR 10 while the reactor effluent from CSTR 10 is, simultaneously with the introduction of the feeds, withdrawn from CSTR 10 through conduit 16.

The reactor effluent is passed from CSTR 10 through conduit 16 to first phase separator 18 which provides means for separating the reactor effluent into an ionic liquid catalyst phase 20 and a hydrocarbon or polyalphaolefin-containing phase 22. The separated ionic liquid catalyst phase 20 is recycled by way of conduit 24 and combined with the makeup ionic liquid catalyst passing through conduit 14 and thereby is introduced into CSTR 10.

The polyalphaolefin-containing phase 22 passes from phase separator 18 through conduit 26 to deactivation vessel 28 which provides means for contacting any remaining ionic liquid catalyst mixed with the polyalphaolefin-containing phase with water so as to deactivate the ionic liquid catalyst. The mixture of polyalphaolefin-containing phase, water and deactivated ionic liquid catalyst passes from deactivation vessel 28 through conduit 30 to second phase separator 32 which provides means for separating the waste water and catalyst phases 34 and polyalphaolefin containing phase 36. The waste water phase passes from second phase separator 32 by way of conduit 37.

The polyalphaolefin-containing phase 36 passes from second phase separator 32 through conduit 38 to water wash vessel 40 which provides means for contacting the polyalphaolefin-containing phase 36 with fresh water. The fresh water is charged to or introduced into water wash vessel 40 through conduit 42. The water and polyalphaolefin-containing phases pass from water wash vessel 40 through conduit 44 to third phase separator 46 which provides means for separating the water and the polyalphaolefin-containing phase introduced therein from water wash vessel 40 into a water phase 48 and polyalphaolefin-containing phase 50. The water phase 48 can be recycled and introduced into deactivation vessel 28 through conduit 52 thereby providing the deactivation wash water for use in the deactivation vessel 28.

The polyalphaolefin-containing phase 50 passes from third phase separator 46 through conduit 54 to water separation vessel 56, which provides means for separating water from the polyalphaolefin-containing phase 50, preferably by flash separation, to provide a flash water stream and a polyalphaolefin-containing phase having a low water concentration. The flash water stream can pass from water separation vessel 56 and recycled to deactivation vessel 28 through conduit 58, or alternatively, the flash water stream can be disposed of as waste water via conduit 37. The polyalphaolefin-containing phase having a low water concentration passes from water separation vessel 56 through conduit 60 and is charged to separation vessel 62, which is preferably an evaporator. Separation vessel 62 provides means for separating the polyalphaolefin-containing phase having a low water concentration into a first stream comprising monomer and, optionally, dimer, and a second stream comprising a polyalphaolefin product. The first stream passes from separation vessel 62 by way of conduit 64 and is recycled to conduit 12 wherein it is mixed with the monomer feed and charged to CSTR 10.

The second stream passes from separation vessel 62 through conduit 64 to guard vessel 66, which defines a zone preferably containing alumina and provides means for removing chlorine and other possible contaminants from the second stream prior to charging it to hydrogenation reactor 68. The effluent from guard vessel 66 passes through conduit 70 to hydrogenation reactor 68. Hydrogenation reactor 68 provides means for reacting the polyalphaolefin product in the second stream to provide a hydrogenated polyalphaolefin product of which a substantial portion of the carbon-carbon double bonds are saturated with hydrogen. Hydrogen is introduced by way of conduit 72 into conduit 70 and mixed with the second stream prior to charging the thus-mixed hydrogen and second stream into hydrogenation reactor 68. The hydrogenated polyalphaolefin product passes from hydrogenation reactor 68 by way of conduit 74.

The following examples of the invention are presented merely for the purpose of illustration and are not intended to limit in any manner the scope of the invention.

EXAMPLES 1-3—Batch Oligomerization of 1-Dodecene

The following Examples 1-3 illustrate the effect of the ionic liquid catalyst concentration on certain of the physical properties of the oligomer reaction product resulting from the batch oligomerization of 1-dodecene.

EXAMPLE 1

400 g of molecular sieve-dried 1-dodecene was added to a three-necked round-bottom flask under a nitrogen purge and heated to 50° C. An addition funnel containing 4.1 g of catalyst (2:1 molar ratio $AlCl_3$:TMA.HCl) was attached to the round-bottom flask. The system was purged with nitrogen and the catalyst was slowly added to the 1-dodecene. The nitrogen purge was continued through the entire reaction. The temperature was controlled with an ice bath and an exotherm (maximum temperature 129° C.) was observed. Samples were pulled every 15 minutes for one hour, neutralized with dilute KOH to quench the catalyst, and filtered through alumina to remove water. Table 1 summarizes the gel permeation chromatography (GPC) results, including the oligomer distribution, weight average molecular weight ($M_w$) and polydispersity index (D) of the sampled product.

TABLE 1

| Product | Units | Example 1a 15 Min. Sample | Example 1b 30 Min. Sample | Example 1c 45 Min. Sample | Example 1d 60 Min. Sample |
|---|---|---|---|---|---|
| Monomer | Weight % | 35.9 | 36.7 | 35.3 | 34.6 |
| Dimer | Weight % | 11.2 | 10.5 | 10.3 | 10.4 |
| Trimer | Weight % | 19.7 | 20.0 | 19.9 | 19.9 |
| Tetramer | Weight % | 10.3 | 10.5 | 10.6 | 10.7 |
| Pentamer + | Weight % | 22.8 | 22.4 | 23.9 | 24.4 |
| Mw | | 497 | 490 | 506 | 514 |
| D | | 1.63 | 1.60 | 1.62 | 1.63 |

After a total reaction time of one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 9.67 cSt, a viscosity index of 132, and a pour point of −42° C.

EXAMPLE 2

The conditions of Example 1 were repeated except that 22.1 g of catalyst were used and the initial reaction temperature was 35° C. The analyses of the samples taken during the reaction are presented in Table 2.

TABLE 2

| Product | Units | Example 2a 15 Min. Sample | Example 2b 30 Min. Sample | Example 2c 45 Min. Sample | Example 2d 60 Min. Sample |
|---|---|---|---|---|---|
| Monomer | Weight % | 50.3 | 47.5 | 46.2 | 41.0 |
| Dimer | Weight % | 1.8 | 1.9 | 1.9 | 2.0 |
| Trimer | Weight % | 5.9 | 6.1 | 6.1 | 6.2 |
| Tetramer | Weight % | 5.1 | 5.5 | 5.4 | 5.6 |
| Pentamer + | Weight % | 37.0 | 39.1 | 40.4 | 45.3 |
| Mw | | 625 | 648 | 676 | 744 |
| D | | 2.21 | 2.20 | 2.25 | 2.28 |

After one hour, the catalyst was removed from the reaction vessel with a syringe. Dilute KOH was then added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 17.7 cSt, a viscosity index of 154, and a pour point of −36° C.

EXAMPLE 3

The conditions of Example 1 were repeated except that 40.1 g of catalyst were used and the initial reaction temperature was 20° C. The analyses of the samples taken during the reaction are presented in Table 3.

TABLE 3

| Product | Units | Example 3a 15 Min. Sample | Example 3b 30 Min. Sample | Example 3c 45 Min. Sample | Example 3d 60 Min. Sample |
|---|---|---|---|---|---|
| Monomer | Weight % | 18.8 | 11.1 | 8.1 | 3.3 |
| Dimer | Weight % | 1.7 | 1.7 | 1.3 | 2.0 |
| Trimer | Weight % | 5.8 | 5.8 | 5.4 | 5.8 |
| Tetramer | Weight % | 5.9 | 6.1 | 5.8 | 6.6 |
| Pentamer + | Weight % | 68.0 | 75.4 | 79.4 | 82.4 |
| Mw | | 1133 | 1257 | 1318 | 1346 |
| D | | 2.12 | 1.84 | 1.70 | 1.45 |

After one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 26.6 cSt, a viscosity index of 172, and a pour point of −30° C.

Examples 1-3 demonstrate that, for the batch oligomerization of 1-dodecene, both the values for the kinematic viscosity and viscosity index of the end product unexpectedly increases with an increase in the ionic liquid catalyst concentration. The pour point temperature of the end-product also increases with increasing catalyst concentration.

Examples 4-6—BATCH OLIGOMERIZATION OF 1-DECENE

The following Examples 4-6 illustrate the effect of ionic liquid catalyst concentration on certain of the physical properties of the oligomerization reaction product resulting from the batch oligomerization of 1-decene.

EXAMPLE 4

The conditions of Example 1 were repeated except that 4.0 g of catalyst were used, 1-decene was substituted for 1-dodecene, and the initial reaction temperature was 50° C. The analyses of the samples taken during the reaction are presented in Table 4.

TABLE 4

| Product | Units | Example 4a 15 Min. Sample | Example 4b 30 Min. Sample | Example 4c 45 Min. Sample | Example 4d 60 Min. Sample |
|---|---|---|---|---|---|
| Monomer | Weight % | | | | 52.0 |
| Dimer | Weight % | | | | 6.5 |
| Trimer | Weight % | | | | 8.4 |
| Tetramer | Weight % | | | | 13.6 |
| Pentamer | Weight % | | | | 4.6 |
| Hexamer | Weight % | | | | 14.9 |
| Mw | | 256 | 256 | 253 | 263 |
| D | | 1.36 | 1.36 | 1.36 | 1.37 |

After one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 8.55 cSt, a viscosity index of 137, and a pour point of −57° C.

EXAMPLE 5

The conditions of Example 4 were repeated except that 22.1 g of catalyst were used and the initial reaction temperature was 35° C. The analyses of the samples taken during the reaction are presented in Table 5.

TABLE 5

| Product | Units | Example 5a 15 Min. Sample | Example 5b 30 Min. Sample | Example 5c 45 Min. Sample | Example 5d 60 Min. Sample |
|---|---|---|---|---|---|
| Monomer | Weight % | | | | 32.5 |
| Dimer | Weight % | | | | 4.0 |
| Trimer | Weight % | | | | 12.0 |
| Tetramer | Weight % | | | | 8.8 |
| Pentamer | Weight % | | | | 10.0 |
| Hexamer + | Weight % | | | | 32.7 |
| Mw | | 400 | 369 | 368 | 464 |
| D | | 1.71 | 1.70 | 1.70 | 1.73 |

After one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity of 14.27 cSt, a viscosity index of 146, and a pour point of −51° C.

EXAMPLE 6

The conditions of Example 4 were repeated except that 40 g of catalyst were used and the initial reaction temperature was 20° C. The analyses of the samples taken during the reaction are presented in Table 6.

TABLE 6

| Product | Units | Example 6a 15 Min. Sample | Example 6b 30 Min. Sample | Example 6c 45 Min. Sample | Example 6d 60 Min. Sample |
|---|---|---|---|---|---|
| Monomer | Weight % | | | | 13.1 |
| Dimer | Weight % | | | | 6.6 |
| Trimer | Weight % | | | | 15.5 |
| Tetramer | Weight % | | | | 15.6 |
| Pentamer | Weight % | | | | 14.6 |
| Hexamer + | Weight % | | | | 34.5 |
| Mw | | 370 | 368 | 367 | 652 |
| D | | 1.80 | 1.82 | 1.81 | 1.58 |

After one hour, dilute KOH was added to the reaction vessel, the contents were stirred and then allowed to phase separate. The hydrocarbon phase was subsequently hydrogenated and finally distilled until the monomer content was less than 1%. The hydrogenated and distilled product had a kinematic viscosity at 100° C. of 18.31 cSt, a viscosity index of 153, and a pour point −48° C.

Examples 4-6 demonstrate that for the batch oligomerization of 1-decene, both the values for the kinematic viscosity and viscosity index of the end product unexpectedly increases with an increase in the ionic liquid catalyst concentration. The pour point temperature of the end product also increases with increasing catalyst concentration.

EXAMPLES 7-9—CONTINUOUS OLIGOMERIZATION of 1-DODECENE

The following Examples 7-9 illustrate the novel continuous process for the manufacture of a high viscosity polyalphaolefin product from a 1-dodecene feedstock using an ionic liquid catalyst. These Examples further illustrate the effect of ionic liquid catalyst concentration on certain of the physical properties of the oligomer reaction product resulting from the continuous process for the oligomerization of 1-dodecene.

EXAMPLE 7

In a continuous process, 1-dodecene was fed at a rate of 50 lbs/hr along with a catalyst feed (1.65:1 molar ratio $AlCl_3$:TMA.HCl) of 0.5 lbs/hr into a 2-gallon stirred-tank reactor with an external cooling loop including a pump and heat exchanger. The cooling loop had a 10 gpm circulation rate. The reactor stirrer was set at a tip speed of 1150 ft/min. The reaction section had a 30-minute residence time and temperature was maintained at 95° F with a pressure of 15 psig. The reactor effluent was quenched with water to deactivate the active catalyst. Oligomer distribution data, molecular weight average ($M_w$) and polydispersity (D) were determined using gel permeation chromatography (GPC) on the resulting reaction product. A sample of the resulting product was distilled to contain less than 1% monomer and hydrogenated in the laboratory. Certain of the physical properties of the distilled and hydrogenated polyalpaolefin product were determined. The properties of the polyalphaolefin product of this Example 7 and of the polyalphaolefin product of the following Examples 8-10 are presented in Table 7 below.

TABLE 7

| Product | Units | Example 7 | Example 8 | Example 9 | Example 10 |
|---|---|---|---|---|---|
| Properties of Reactor Effluent | | | | | |
| Monomer | Weight % | 44.3 | 0.3 | 47.7 | 0.8 |
| Dimer | Weight % | 1.0 | 0.4 | 0.6 | 0.7 |
| Trimer | Weight % | 3.7 | 1.8 | 2.5 | 2.1 |
| Tetramer | Weight % | 3.8 | 3.1 | 2.7 | 3.2 |
| Pentamer | Weight % | 5.5 | 4.9 | 4.1 | 4.7 |
| Hexamer | Weight % | 5.0 | 5.3 | 4.0 | 5.4 |
| Heptamer + | Weight % | 36.7 | 84.3 | 38.5 | 83.1 |
| Mw | | 851 | 1796 | 748 | 1649 |
| D | | 2.70 | 1.67 | 2.88 | 1.41 |
| Properties of Distilled and Hydrogenated Product | | | | | |
| 100° C. Viscosity | cSt | 18.6 | 32.3 | | 22.1 |
| Viscosity Index | | 156 | 157 | | 151 |
| Pour Point | ° C. | −36 | −36 | | −45 |

EXAMPLE 8

The conditions for Example 7 were repeated with the exception of the catalyst feed rate which was 4 lb/hr. The polyalphaolefin product was obtained as described in Example 7, the properties of which are presented in Table 7.

EXAMPLE 9

The conditions for Example 7 were repeated with the exception of the reaction temperature which was 70° F. The polyalphaolefin product was obtained as described in Example 7, the properties of which are presented in Table 7.

Examples 7-9 demonstrate that a high viscosity polyalphaolefin product having desirable physical properties can be manufactured using a continuous process for the ionic liquid catalyzed oligomerization of an alpha olefin monomer. The Examples also demonstrate that the values for the kinematic viscosity and viscosity index of the end product from the continuous oligomerization of 1-decene increase with increasing concentration of ionic liquid catalyst. An oligomer end-product having a significantly high kinematic viscosity is obtainable from the continuous process.

EXAMPLE 10—CONTINUOUS OLIGOMERIZATION OF 1-DECENE

This Example 10 illustrates the novel continuous process for the manufacture of a high viscosity polyalphaolefin product from a 1-decene feedstock using an ionic liquid catalyst.

EXAMPLE 10

The conditions for Example 7 were repeated with the exception of the catalyst feed rate which was 1.3 lb/hr and the feed was 1-decene. The resulting product was then processed in batch operation to flash out the monomer and to hydrogenate the end product. Certain of the physical properties of the polyalphaolefin product were determined. These physical properties are presented in Table 7.

Example 10 further demonstrates that a high viscosity polyalphaolefin product having desirable physical properties can be manufactured using a continuous process for the ionic liquid catalyzed oligomerization of an alpha olefin monomer. An oligomer end product having a high kinematic viscosity is obtainable from the continuous process.

EXAMPLES 11-12—CONTROLLING WATER IN REACTION

EXAMPLE 11

In a continuous process, 1-decene was fed at a rate of 2786 g/hr along with a catalyst feed (1.65:1 molar ratio $AlCl_3$:TMA.HCl) of 59.3 g/hr into a 1-gallon stirred-tank reactor with an internal cooling coil and a recirculation loop with a mixing pump. The reactor stirrer speed was set at 660 rpm. The reaction section had a 31-minute residence time and temperature was maintained at 40° C. with a nitrogen pressure of 31 psig. The reactor effluent was quenched with water to deactivate the active catalyst. The resulting 1-decene conversion was 36.2%.

EXAMPLE 12

This example illustrates how moisture in the nitrogen affects 1-decene conversion. In a continuous process, 1-decene was fed at a rate of 2928 g/hr along with a catalyst feed (1.65:1 molar ratio $AlCl_3$:TMA.HCl) of 51.1 g/hr into a stirred-tank reactor. The reactor configuration was identical to that described in Example 11, except the nitrogen headspace gas in the reactor was sparged through a water tank at a rate of 0.5 SCFH. The reactor stirrer speed was set at 400 rpm. The reaction section had a 36-minute residence time and temperature was maintained at 40° C. The resulting 1-decene conversion was 68.3%.

EXAMPLE 13

This example illustrates that the polyalphaolefins of the inventive process do not have a regular repeating structure of a polyalphaolefin produced by head-to-tail oligomerization. The polyalphaolefin was produced by the continuous oligomerization of 1-decene. The reactor effluent was distilled to contain less than 1% monomer and hydrogenated and then analyzed by infrared spectroscopy and $^{13}C$ spectroscopy. From these spectra the branching index, number of methyl groups, and the percent short chain branching was determined. These values are present in Table 8.

TABLE 8

|  | Infrared Spectroscopy | $^{13}C$ NMR Spectroscopy |
|---|---|---|
| Branch Ratio | 0.19 | .143 |
| Number of methyl groups | — | >6 |
| Percent short chain branching | — | 23.6 |

Figure 4:
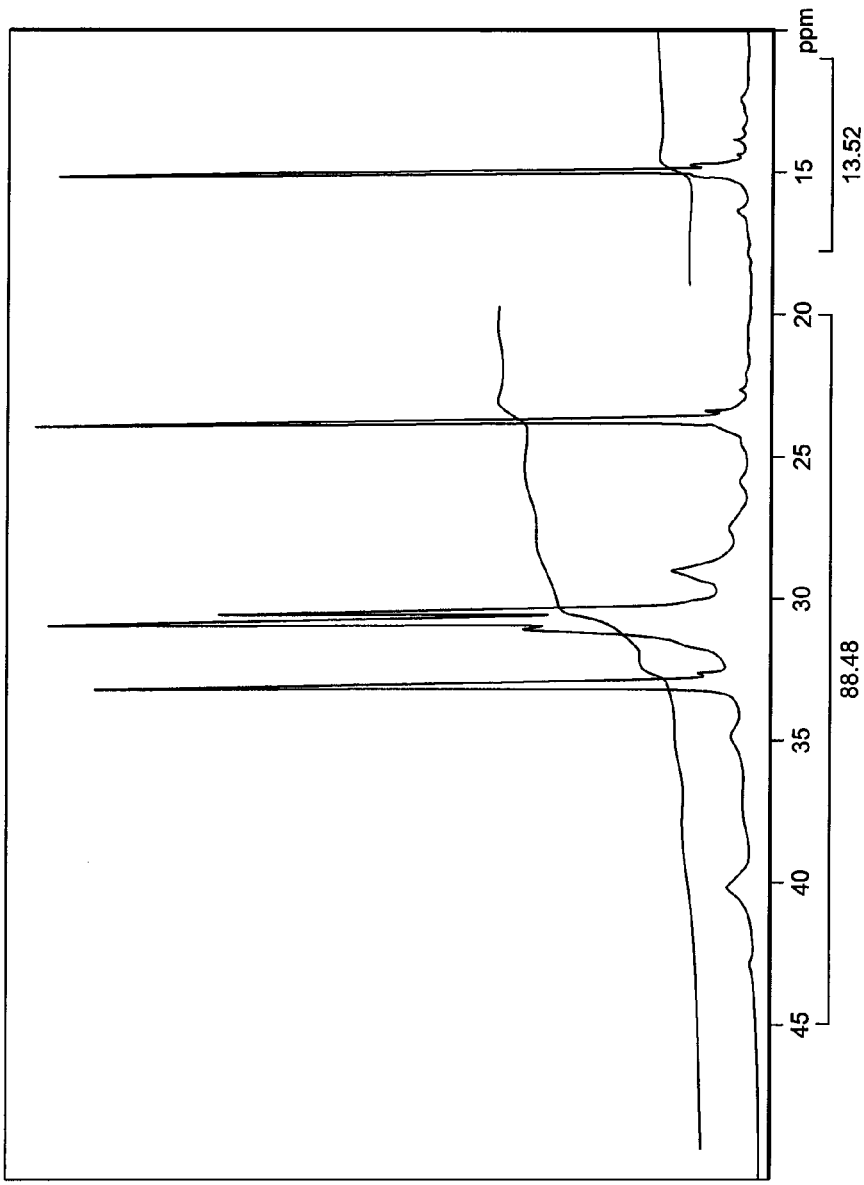
FIG. 4 is a 10-50 ppm 13C NMR spectrum of a polyalphaolefin product produced from 1-decene by the inventive process.
Figure 5:
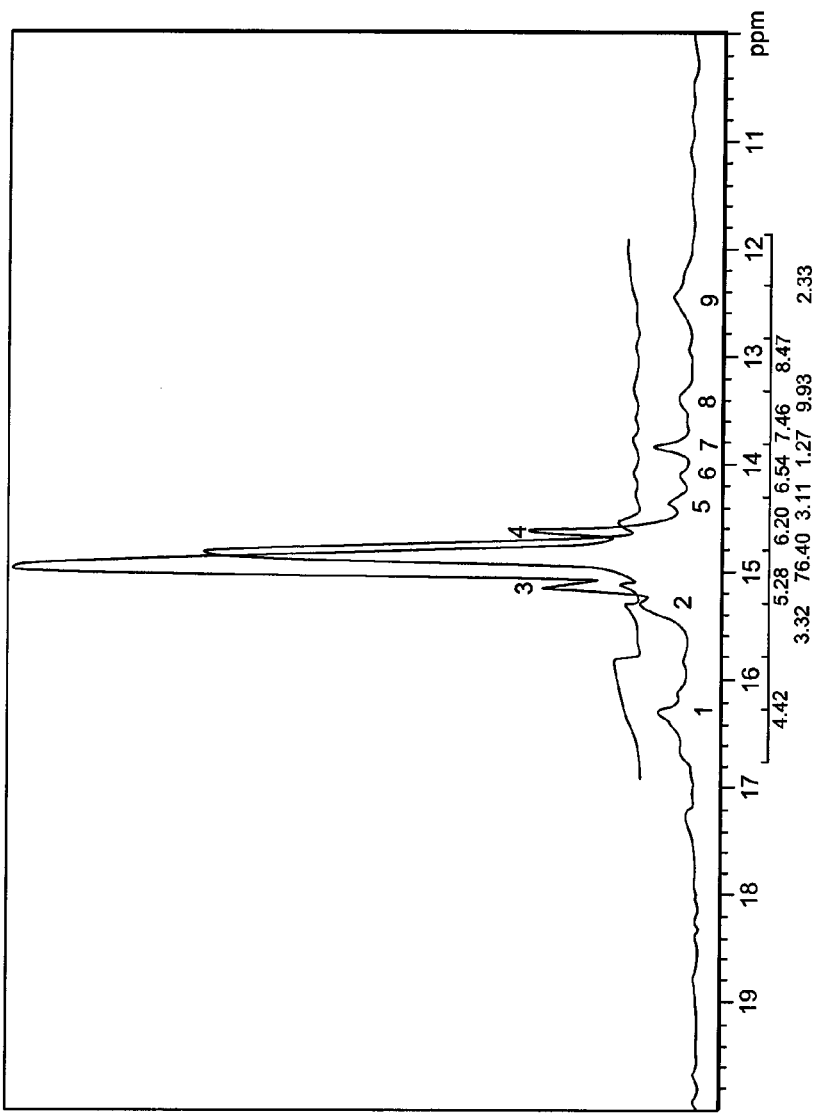
FIG. 5 is a 10-20 ppm 13C NMR spectrum of a polyalphaolefin product produced from 1-decene by the inventive process.

The Infrared Spectroscopy Branch ratio was determined by the method discussed in "Standard Hydrocarbon of High Molecular Weight", Analytical Chemistry, Vol. 25 no. 10 pp. 1466-1470 (1953). The $^{13}C$ NMR percent short chain branching was determined by integrating the methyl region of the a $^{13}C$ NMR (10-20 ppm) and the equation:

$$\text{Percent Short Chain Branching} = \frac{100 * \sum {}^{13}C \text{ integrals of short chain methyl groups}}{\sum {}^{13}C \text{ integrals of all methyl groups}}$$

wherein the long chain methyl group is represented by the largest and most predominant methyl group. The $^{13}C$ NMR branch ratio was determined by integrating the methyl, methylene and methine region of the PAO's $^{13}C$ NMR spectra. The $^{13}C$ NMR branch ratio was then calculated using the formula:

$$^{13}C \text{ Branch Ratio} = \frac{15 * \sum {}^{13}C \text{ integrals } 11-15 \text{ ppm}}{(15 * \sum {}^{13}C \text{ integrals } 11-15 \text{ ppm}) + (14 * \sum {}^{13}C \text{ integrals } 19.5-44.5 \text{ ppm})}$$

wherein the methyl group integrals was summed over the range of 11-15 ppm and the methylene and methine group integrals was summed over the range 19.5-44.5 ppm. FIGS. 4 and 5 represent the $^{13}C$ spectra used to determine the values present in Table 8. Additionally, FIG. 5 counts the number of different short chain branches with a numeral above or below each short chain branch methyl group.

EXAMPLE 14

A catalyst mixture was prepared using a 2 to 1 ratio of aluminum trichloride to trimethylamine hydrochloride. The catalyst (39.2 g) was placed in a 1 liter round bottom flask to which 401.2 g of 1-decene was added dropwise. The initial temperature of the oligomerization mixture was 0° C. which was allowed to raise to 22° C. An inert atmosphere was maintained by a nitrogen sweep gas/bubbler. The reaction was allowed to proceed for 1 hour and was quenched with aqueous potassium hydroxide. The product was water washed and hydrogenated using a nickel catalyst. The residual monomer and dimer were:

| 100° C. Kinematic Viscosity | 31.6 cSt |
|---|---|
| 40° C. Kinematic Viscosity | 283 cSt |
| Viscosity Index | 152 |
| Pour Point | −39° C. |
| Noack Volatility | 1.68% |

EXAMPLE 15

The general procedure was the same as in Example 14, above, except for the addition of 185 grams of heptane diluent which was mixed with 400 grams of decene. Catalyst was prepared in a 2 to 1 molar ratio of aluminum trichloride to trimethylamine hydrochloride and 40.1 grams were added to the reaction in a dropwise manner. The initial reaction temperature was −60° C. The product was water washed and hydrogenated using a nickel catalyst. The residual monomer and dimer were removed by distillation to less than 1%. The distilled oligomer was found to display the following properties:

| 100° C. Kinematic Viscosity | 15.0 cSt |
|---|---|
| 40° C. Kinematic Viscosity | 109 cSt |
| Viscosity Index | 143 |
| Pour Point | −45° C. |

It should be noted that the kinematic viscosity of the oligomer of Example 15 was significantly less at both 100° C. and 40° C. than that for the oligomer of Example 14. The viscosity index of the product of Example 15 was also lower.

Although the invention has been described in detail and with preferred embodiments, it is to be understood that modifications and variations may be resorted to, without departing from the spirit and scope of the invention. Such modifications and variations are considered to be within the provisions and scope of the appended claims.

That which is claimed is:

1. A process for producing a polyalphaolefin product, comprising:
   (a) contacting, in an absence of an organic diluent, a feed consisting essentially of one or more high purity Normal Alpha Olefin fraction having from 4 to 14 carbon atoms with an ionic liquid oligomerization catalyst, wherein the high purity Normal Alpha Olefin in the feed comprises at least 95 weight percent of the feed;
   (b) maintaining the feed and the ionic liquid oligomerization catalyst under preselected conditions for a sufficient time to oligomerize the feed to the polyalphaolefin product; and
   (c) recovering the polyalphaolefin product.

2. The process of claim 1 wherein the ionic liquid oligomerization catalyst comprises an acidic ionic liquid catalyst.

3. The process of claim 2 wherein the acidic ionic liquid catalyst comprises a first component and a second component:
   wherein the first component comprises a compound selected from the group consisting of aluminum halide, alkyl aluminum halide, gallium halide, and alkyl gallium halide; and wherein the second component is a quaternary ammonium, quaternary phosphonium, or quaternary sulfonium salt.

4. The process of claim 2 wherein the acidic ionic liquid catalyst comprises a first component and a second component;
   wherein the first component comprises a compound selected from the group consisting of a titanium halide and an alkyl titanium halide; and
   wherein the second component is a quaternary ammonium, quaternary phosphonium or quaternary sulfonium salt.

5. The process of claim 1 wherein the feed consists essentially of one or more high purity Normal Alpha Olefin fraction having from 8 to 12 carbon atoms.

6. The process of claim 1 wherein the polyalphaolefin product has a viscosity of not less than 22 centistokes at 100° C.

7. The process of claim 1 wherein the polyalphaolefin product has a pour point of less than −30° C.

8. The process of claim 1 wherein the polyalphaolefin product has a dimer content of less than 2 weight percent.

9. A method of making a polyalphaolefin product, comprising:
   (a) contacting, in an absence of an organic diluent, a monomer feed comprising one or more high purity Normal Alpha Olefin having from 6 to 20 carbon atoms with an ionic liquid oligomerization catalyst, wherein the high purity Normal Alpha Olefin in the monomer feed comprises at least 95 weight percent of the monomer feed;
   (b) maintaining the feed and the ionic liquid oligomerization catalyst under preselected conditions for a sufficient time to oligomerize the feed to the polyalphaolefin product; and
   (c) recovering the polyalphaolefin product.

10. The method of claim 9 wherein the monomer feed comprises one or more high purity Normal Alpha Olefin having from 6 to 14 carbon atoms.

11. The method of claim 9 wherein the polyalphaolefin product has a kinematic viscosity of not less than 22 centistokes at 100° C.

12. The method of claim 9 wherein the polyalphaolefin product has a polydispersity index of from 1.0 to 3.5.

13. The method of claim 9 wherein the polyalphaolefin product has a pour point of less than or equal to −30° C. according to ASTM D97.

14. The method of claim 9 wherein the polyalphaolefin product has a viscosity index greater than 130.

15. The method of claim 9 wherein the polyalphaolefin product has a bromine index of less than or equal to 800 mg/100 g according to ASTM D2710.

16. The method of claim 9 wherein the polyalphaolefin product has a branch ratio greater than or equal to 0.19.

17. The method of claim 9 wherein the polyalphaolefin product has a branch ratio that exceeds a theoretical branch ratio of polyalphaolefins produced by methods giving regular head to tail oligomerization by 15 percent.

18. The method of claim 9 wherein the polyalphaolefin product has at least 3 percent short chain branching.

19. The method of claim 9 wherein the polyalphaolefin product has a dimer content of less than 2 weight percent.

20. The method of claim 9 wherein the polyalphaolefin product has a weight average molecular weight in the range of from 250 to 3000.

21. The method of claim 9 wherein polyalphaolefin product comprises at least 2 different short chain branches observable by 13C NMR.

22. The method of claim 9 wherein a weight ratio of the ionic liquid catalyst to the feed is in the range upwardly to 1:1.

23. The method of claim 9 wherein a concentration of water in the feed is from 5 to 15 ppm based upon the weight of the feed.

24. The method of claim 9 wherein the ionic liquid oligomerization catalyst is formed by a combination of a metal halide and a liquid salt comprising quaternary ammonium, quaternary phosphonium, or quaternary sulfonium.

25. The method of claim 9 wherein the polyalphaolefin product comprises trimers, tetramers, higher oligomers, polymers, or a mixture of any one or more thereof.

* * * * *